(12) United States Patent
Bohanon

(10) Patent No.: US 6,251,869 B1
(45) Date of Patent: Jun. 26, 2001

(54) ENHANCEMENT OF OXAZOLIDINONE ANTIBACTERIAL AGENTS ACTIVITY BY USING ARGININE DERIVATIVES

(75) Inventor: Michael John Bohanon, Gobles, MI (US)

(73) Assignee: Pharmacia & Upjohn Company, Kalamazoo, MI (US)

(*) Notice: Subject to any disclaimer, the term of this patent is extended or adjusted under 35 U.S.C. 154(b) by 0 days.

(21) Appl. No.: 09/313,465

(22) Filed: May 17, 1999

Related U.S. Application Data

(63) Continuation-in-part of application No. 09/081,164, filed on May 18, 1998, now abandoned.

(51) Int. Cl.[7] .................... A61K 38/00; A61K 31/535
(52) U.S. Cl. .................... 514/20; 514/19; 514/237.5; 514/255.01; 514/336; 514/350; 514/376; 562/560
(58) Field of Search ............... 514/19, 20, 237.5, 514/255.01, 336, 376, 350; 562/560

(56) References Cited

U.S. PATENT DOCUMENTS

| | | | |
|---|---|---|---|
| 5,977,373 | * 11/1999 | Gadwood et al. | 548/128 |
| 5,989,832 | * 11/1999 | Trias et al. | 435/7.2 |
| 6,998,406 | * 12/1999 | Hestter, Jr. | 514/218 |

FOREIGN PATENT DOCUMENTS

| | | | |
|---|---|---|---|
| WO99/17791 | 4/1999 | (WO) | A61K/38/06 |

OTHER PUBLICATIONS

Barbachyn et al. J. Med. Chem. vol. 39, No. 3 pp. 680–685, Feb. 1996.*

Brickner et al. J. Med. Chem. vol. 39, No. 3 pp. 673–679, Feb. 1996.*

* cited by examiner

*Primary Examiner*—Bennett Celsa
(74) *Attorney, Agent, or Firm*—Lucy X. Yang

(57) ABSTRACT

The present invention provides methods and compositions for enhancing the effectiveness of oxazolidinone antibacterial agents against gram-negative organisms infection by using an arginine derivative.

15 Claims, No Drawings

ENHANCEMENT OF OXAZOLIDINONE ANTIBACTERIAL AGENTS ACTIVITY BY USING ARGININE DERIVATIVES

CROSS-REFERENCE TO RELATED APPLICATIONS

This application is a continuation of application which is currently being converted under 37 CFR 1.53(c)(2) from U.S. Pat. Ser. No. 09/081,164, filed May 18, 1998, now abandoned.

FIELD OF THE INVENTION

The present invention relates to methods and compositions for enhancing the effectiveness of oxazolidinone antibacterial agents against gram-negative organisms by using an arginine derivative.

BACKGROUND OF THE INVENTION

The oxazolidinone antibacterial agents are a novel synthetic class of antimicrobials with potent activity against a number of human and veterinary pathogens, including gram-positive aerobic bacteria such as multiply-resistant staphylococci and streptococci, anaerobic organisms such as bacteroides and clostridia species, and acid-fast organisms such as *Mycobacterium tuberculosis* and *Mycobacterium avium*. In particular, the oxazolidinone compounds of structures I–V have been found especially effective.

I

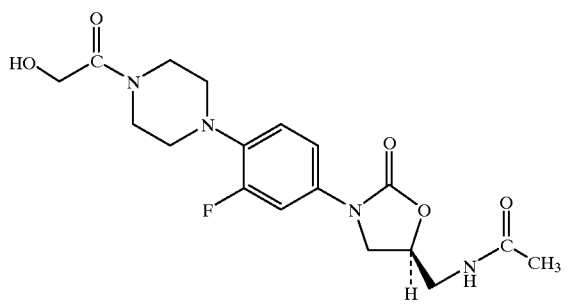

II

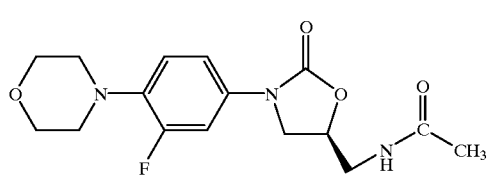

III

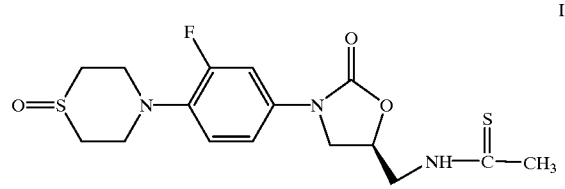

IV

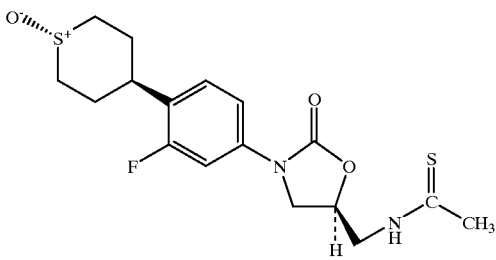

V

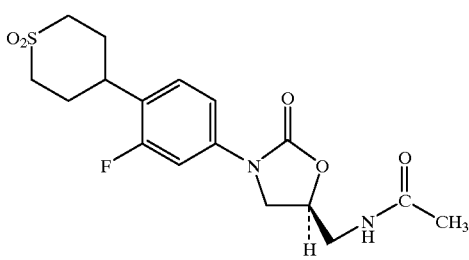

However, certain oxazolidinones generally have poor activity at a useful level against aerobic gram-negative organisms such as *E. coli, Haemophilus influenzae, Moraxella catarrhalis, Pseudomonas aeruginosa,* or *Klebsiella pneumoniae*. Thus, the use of these oxazolidinone antibacterial agents alone is limited to infectious states due to gram-positive bacteria. Accordingly, it is among the objects of the present invention to provide a process for enhancing the inhibitory spectrum of the oxazolidinones. We have now discovered that when the oxazolidinone antibacterial agents are administered with an arginine derivative, a pronounced synergic effect against gram-negative organisms is produced. The effective amount of an oxazolidinone antibacterial agent to be fully efficacious against aerobic gram-negative organisms is much lower than would be needed if an oxazolidinone was administered without these arginine derivatives.

INFORMATION DISCLOSURE

International publication No. WO 96/33285 discloses methods for screening inhibitors of microbial efflux pumps, including those which export antibiotics. The screening methods are based on the increase in the intracellular concentration of a compound, such as an antibiotic or a dye, when the bacterial cells are contacted with an efflux pump inhibitor. In addition, this invention provides pharmaceutical compositions containing such efflux pump inhibitors, including certain arginine derivatives, and methods for treating microbial infections and enhancing the antimicrobial activity of certain antimicrobial agents.

The abstract of the 36th ICAAC, presented by Pharmacia and Upjohn, Inc. discloses mutation of the AcrAB antibiotic efflux pump in *E. coli* confers susceptibility to oxazolidinone antibacterial agents.

SUMMARY OF THE INVENTION

The present invention presents a method and a composition for treating gram-negative organisms infections in mammal which comprises administration of an effective amount of an oxazolidinone antibacterial agent and an arginine derivative of formula A

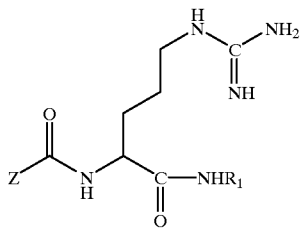

wherein
R₁ is
  a) aryl, optionally substituted with $C_{1-4}$ alky, $C_{1-4}$ alkoxy, $C_{1-4}$ alkythio, halo, or —$NH_2$,
  b) —$(CH_2)_i$—aryl, in which aryl is substituted with $C_{1-4}$ alkyl, $C_{1-4}$ alkoxy, $C_{1-4}$ alkythio, halo, or —$NH_2$,
  c) thienyl, furyl, pyridyl, benzofuranyl, or benzothienyl;
Z is $R_2$, or —$CHWR_2$;
$R_2$ is
  a) aryl, optionally substituted with one or two $C_{1-4}$ alkyl, $C_{1-4}$ alkoxy, $C_{1-4}$ alkythio, halo, —$NH_2$, $C_{1-4}$ alkylamino, $C_{1-4}$ dialkylamino, or —NHOH,
  b) $C_{1-4}$ alkyl, optionally substituted with fluoro,
  c) $C_{1-4}$ alkoxy, $C_{1-4}$ alkythio,
  d) halo,
  e) thienyl, furanyl, or pyridyl;
W is H, —$NH_2$, $C_{1-4}$ alkylamino, $C_{1-4}$ dialkylamino, halo, hydroxyl, $C_{1-4}$ alkoxy, alkylthio, or azaheterocycle;
aryl is phenyl, or naphthyl;
azaheterocycle is n-morpholinyl, n-piperazinyl, n-pyrrolidinyl, n-imidazolyl, n-pyrrolyl, n-pyrazolyl, n-triazolyl, or n-tetrazolyl;
i is 0, 1, or 2; and pharmaceutically acceptable salts.

DETAILED DESCRIPTION OF THE INVENTION

The present invention teaches that when oxazolidinone antibacterial agents are administered with an arginine derivative, the oxazolidinones are effective against aerobic gram-negative organisms such as *E. coli, Haemophilus influenzae, Moraxella catarrhalis, Pseudomonas aeruginosa,* or *Klebsiella pneumoniae,* as well as gram-positive aerobic bacteria such as multiply-resistant staphylococci and streptococci, anaerobic organisms such as bacteroides and clostridia species, and acid-fast organisms such as *Mycobacterium tuberculosis* and *Mycobacterium avium.* The effective amount of an oxazolidinone antibacterial agent to be fully efficacious against aerobic gram-negative organisms is much lower than would be needed if an oxazolidinone was administered without these arginine derivatives.

For the purpose of the present invention, the term "$C_{1-4}$ alkyl" refers to an alkyl group having one to four carbon atoms, such as, methyl, ethyl, propyl, butyl and their isomeric forms thereof.

The term "$C_{1-4}$ alkoxy" refers to an alkyl group having one to four carbon atoms attached to an oxygen atom of hydroxyl group, such as, methoxy, ethoxy, propyloxy, butyloxy and their isomeric forms thereof.

The term "$C_{1-4}$ alkythio" refers to an alkyl group having one to four carbon atoms and isomeric forms thereof attached to a sulfur atom.

The term "$C_{1-4}$ alkylamino" refers to an alkyl group having one to four carbon atoms attached to an amino moiety; for example, methylamino, ethylamino, n-propylamino, n-butylamino and isomeric forms thereof.

The term "$C_{1-4}$ dialkylamino" refers to two alkyl groups having one to four carbon atoms attached to an amino moiety; for example, dimethylamino, methylethylamino, diethylamino, dipropylamino, methypropylamino, ethylpropylamino, dibutylamino and isomeric forms thereof.

The term halo refers to fluoro, chloro, bromo, or iodo, preferably fluoro, chloro, or bromo.

The term "aryl" refers to phenyl or naphthyl;

The term "azaheterocycle" refers to n-morpholinyl, n-piperazinyl, n-pyrrolidinyl, n-imidazolyl, n-pyrrolyl, n-pyrazolyl, n-triazolyl, or n-tetrazolyl;

The term "pharmaceutically acceptable salts" refers to salts useful for administering the compounds of this invention and include hydrochloride, hydrobromide, hydroiodide, sulfate, phosphate, acetate, propionate, lactate, mesylate, maleate, malate, succinate, tartrate, citrate, 2-hydroxyethyl sulfonate, fumarate and the like. These salts may be in hydrated form.

The term "mammal" refers to man or animals of veterinary interest.

Oxazolidinone antibacterial agents refer to compounds of formula B

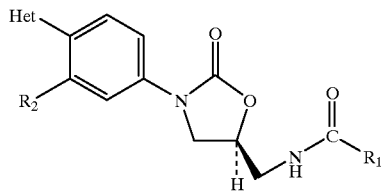

wherein $R_1$ is methyl, ethyl, cyclopropyl, or dichloromethyl; $R_2$ is hydrogen or fluoro; Het is a 6-membered saturated heterocyclic moiety having one to two atoms selected from the group consisting of sulfur, nitrogen and oxygen atoms. Optionally, the nitrogen atom of the heterocyclic may be substituted by a suit group such as hydroxyacetyl, and the sulfur atom may be oxidized. In addition, the compound of formula Y embraces all possible stereoisomers and geometric forms. Preferably, the oxazolidinone antibacterial agents are the compounds of formulas I–V as identified above.

There are numerous references in the art disclosing a variety of oxazolidinone derivatives and the methods of making them. The above oxazolidinone antibacterial agents may be made according to the procedures described in U.S. Pat. Nos. 5,652,238 and 5,688,792, International Publications Nos. WO 93/23384, WO 97/09328 and WO 98/54161, incorporated herein by reference.

Arginine derivatives of formula A are known and readily available or may be prepared by synthetic chemistry methods known to those skilled in the arts. Preferably, arginine derivatives of formula A is L-phenylalanyl-Larginyl-β-naphthylamide.

The pharmaceutical compositions of this invention comprise an oxazolidinone antibacterial agent and an arginine derivative of formula A, together with one or more solid or liquid pharmaceutically acceptable carriers and optionally pharmaceutically acceptable adjuvants and excipients. Solid form compositions include powders, tablets, dispersible granules, capsules and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water, water-propylene glycol, and water-polyethylene glycol systems, optionally containing conventional coloring agents, flavoring agents, stabilizers and thickening agents.

The pharmaceutical compositions are provided by employing conventional techniques. Preferably the compositions are in unit dosage form containing an effective amount of an oxazolidinone antibacterial agent the compounds of formula B.

The amount of an oxazolidinone antibacterial agent in the pharmaceutical composition and unit dosage form thereof may be varied or adjusted widely depending upon the particular application method, the potency of the particular compound, the condition to be treated and the desired concentration. Generally, the quantity of an oxazolidinone antibacterial agent will range between 0.5% to 90% by weight of the total composition.

In therapeutic use for treating bacterial infections in humans and other animals that have been diagnosed with aerobic gram-negative organisms infections, the oxazolidinone antibacterial agent and arginine derivatives or pharmaceutical compositions of the present invention thereof will be administered orally, parenterally, transdermally and/or topically at a dosage to obtain and maintain a concentration, that is, an amount, or blood-level of active component in the animal undergoing treatment which will be antibacterially effective. The preferred form of administration is orally. Generally, such antibacterially effective amount of dosage of active oxazolidinone antibacterial agent will be in the range of about 0.1 to about 100 mg/kg normal body weight, more preferably about 3.0 to about 50 mg/kg of body weight/day. It is to be understood that the dosages may vary depending upon the requirements of the patient, the severity of the bacterial infection being treated, and the particular compounds being used. Also, it is to be understood that the initial dosage administered may be increased beyond the above upper level in order to rapidly achieve the desired blood-level, or the initial dosage may be smaller than the optimum, and the daily dosage may be progressively increased during the course of treatment depending on the particular situation. If desired, the daily dose may also be divided into multiple doses for administration, e.g., two to four times per day.

The amount of an arginine derivative of formula A to be used varies with the enhancing activity of the particular arginine derivative and its absorption by the organism being treated. Sufficient amounts of the arginine derivatives should be used to make aerobic gram-negative organisms susceptible to a pharmaceutically acceptable level of an oxazolidinone antibacterial agent in mammals being treated. The sufficient amount of a particular arginine derivative can simply be determined by testing for minimum inhibitory concentration (MIC) of an oxazolidinone antibacterial agent, and comparing the MIC of that antibacterial agent alone, with the MIC of that antibacterial agent used in combination with the arginine derivative. Generally, the molar ratio of an arginine derivative to an oxazolidinone antibacterial agent which is administered may be from about 0.01 to 10, preferably from about 0.1 to 1.0. Therefore, the daily dosage of an arginine derivative for enhancing the effectiveness of oxazolidinone antibacterial agents against aerobic gram-negative organisms in mammals may range from about 0.01 to 100 mg/kg normal body weight, preferably in an amount of about 0.3 to 50 mg/kg body weight. The arginine derivatives may be administered one to four hours before the oxazolidinone antibacterial agents is administered, or is administered simultaneously with the oxazolidinone antibacterial agents.

BIOLOGICAL TESTING

The potentiation of oxazolidinone antibacterial agents activity against aerobic gram-negative organisms when combined with an arginine derivative of formula A uses two assay techniques:

a) conventional checkerboard technique, and
b) silicone-oil centrifugation method for quantitating an radiolabelled oxazolidinone antibacterial agent in *E. coli*.

I. Determination of Fractional Inhibitory Concentration (FIC) Index by Using Checkerboard Technique.

The "checkerboard" method is the *in vitro* technique used most often to assess antimicrobial combinations (Lorian, V., editor. Antibiotics in Laboratory Medicine, Third Edition, p. 432, Williams & Wilkins. Baltimore, Md. 21202, USA). In the microdilution method, a checkerboard pattern is formed in the wells of microtiter plates that contains multiple 2-fold dilutions of the two agents being tested. The test dilutions span a range of concentrations that are above and below the Minimum Inhibitory Concentration (MIC) of each test agent for the test organism. The response at each test ratio (growth or no growth) is used for the calculation of the Fractional Inhibitory Concentration (FIC) Index. The drug-drug interaction is defined as Additive when the result for the two drugs together is equal to the sum of the results for each of the two drugs used separately (FIC Index=1.0). The interaction is described as Antagonism when the result for the two drugs is significantly less than the Additive response (FIC Index>1.0). The interaction is described as synergistic when the result for the two drugs combined is significantly greater than the Additive response (FIC Index £0.50).

II Quantitating a Radiolabelled Oxazolidinone Antibacterial agent of Formula I Accumulation in *E. coli*. Following Pre-Treatment of the Bacterial Cells with an Arginine Derivative of Formula A.

Measurement of radiolabelled oxazolidinone antibacterial agent of formula I accumulation in *E. coli* was conducted according to the procedures described by Thanassi, D. G., G. S. B. Suh, H. Nikaido, J. Bacteriology, 1995, p. 177, (4):998–1007. Briefly, cells were grown to mid log ($OD_{530}$ 0.5–0.7) in LB/0.2% glucose at 37° C., harvested by centrifugation, washed twice and resuspended to an $OD_{530}$ of 8.0 in 50 mM potassium phosphate pH 7.0,1 mM $MgSO_4$ and 0.2% glucose. 1.0 ml aliquots of the cell suspension were preincubated at 37° C. for 10 minutes prior to the addition of an arginine derivative. Carbonyl cyanide m-chlorophenylhydrazone (CCCP) was used as the positive control. After addition of an arginine derivative, L-phenylalanyl-Larginyl-naphthylamide, the cells were incubated for 30 minutes before the addition of the radiolabelled oxazolidinone antibacterial agent of formula I to a final concentration of 25 TM. The cells were then incubated for an additional 15 minutes. A 50 Tl aliquot was removed and layered on a 300 Tl silicone oil cushion (70% fluid no. 550 and 30% fluid no. 510 silicone oil, Dow Corning Corp. Midland, Mich.). Tubes were centrifuged at 12,000 rpm for 3 minutes, 22° C., then frozen by emersion into liquid $N_2$. The tips of each tube containing the cell pellets were cut off and placed in scintillation vials. After thawing, the cell pellets were suspended in 200 Tl distilled water and 4 ml of scintillation fluid was added. The samples were mixed well and counted in a liquid scintillation counter. To correct for nonspecific adherence of the labelled drug to the cell surface, a control experiment was done with cells incubated throughout with only the addition of vehicle and radiolabelled oxazolidinone antibacterial agent of formula I.

III. RESULTS

The oxazolidinone antibacterial agent of formula I alone demonstrated very poor antibacterial activity, requiring a concentration of 256 mg/ml to inhibit *E. coli* 31700. L-Phenylalanyl-Larginyl-β-naphthylamide alone also demonstrated very poor antibacterial activity as evidenced by no growth inhibition up to a concentration of 256 mg/ml. However, when the two agents were combined in the "checkerboard" pattern, there was dramatic evidence of the potentiation of the activity of oxazolidinone antibacterial agent of formula I by L-phenylalanyl-Larginyl-β-naphthylamide. For example, in the presence of 16 mg/ml L-phenylalanyl-Larginyl-β-naphthylamide, an oxazolidinone antibacterial agent of formula I concentration of 16 mg/ml was inhibitory for bacterial growth. Calculation of the FIC Index yielded a value of 0.23, clearly indicative of a synergistic interaction.

What is claimed is:

1. A method for treating gram-negative organisms infections in mammal which comprises administration of an effective amount of an oxazolidinone antibacterial agent and an arginine derivative of formula A

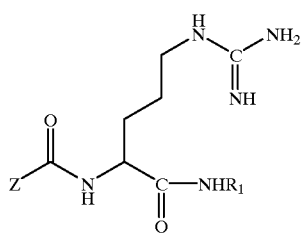

wherein $R_1$ is
  a) aryl, optionally substituted with $C_{1-4}$ alkyl, $C_{1-4}$ alkoxy, $C_{1-4}$ alkythio, halo, or —$NH_2$,
  b) —$(CH_2)_i$—aryl, in which aryl is substituted with $C_{1-4}$ alkyl, $C_{1-4}$ alkoxy, $C_{1-4}$ alkythio, halo, or —$NH_2$, or
  c) thienyl, furyl, pyridyl, benzofuranyl, or benzothienyl;
Z is $R_2$, or —$CHWR_2$;
$R_2$ is
  a) aryl, optionally substituted with one or two $C_{1-4}$ alkyl, $C_{1-4}$ alkythio, halo, —$NH_2$, $C_{1-4}$ alkylamino, $C_{1-4}$ dialkylamino, or —NHOH,
  b) $C_{1-4}$ alkyl, optionally substituted with fluoro,
  C) $C_{1-4}$ alkoxy,
  d) $C_{1-4}$ alkythio,
  e) halo, or
  f) thienyl, furanyl, or pyridyl;
W is H, —$NH_2$, $C_{1-4}$ alkylamino, $C_{1-4}$ dialkylamino, halo, hydroxyl, $C_{1-4}$ alkoxy, $C_{1-4}$ alkylthio, or azaheterocycle;
aryl is phenyl, or naphthyl;
azaheterocycle is n-morpholinyl, n-piperazinyl, n-pyrrolidinyl, n-imidazolyl, n-pyrrolyl, n-pyrazolyl, n-triazolyl, or n-tetrazolyl;
i is 0, 1, or 2;

wherein the oxazolidinone is a compound of structure V–A

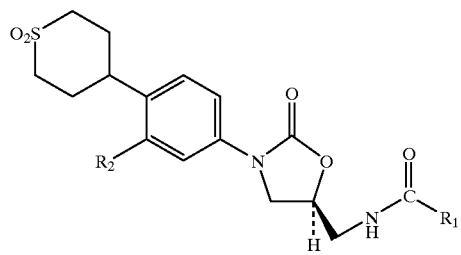

wherein $R_1$ is methyl, ethyl, cyclopropyl, or dichloromethyl;
$R_2$ is hydrogen or fluoro;
and a pharmaceutically acceptable salt.

2. The method of claim 1 in the oxazolidinone which is a compound of structure V

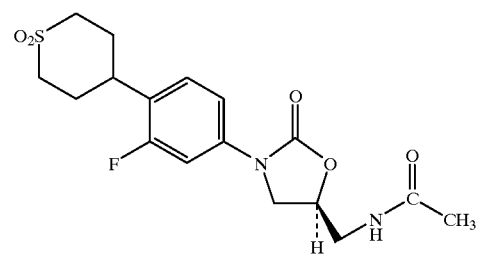

and a pharmaceutically acceptable salt.

3. A method for treating gram-negative organisms infections in mammal which comprises administration of an effective amount of an oxazolidinone antibacterial agent and an arginine derivative of formula A

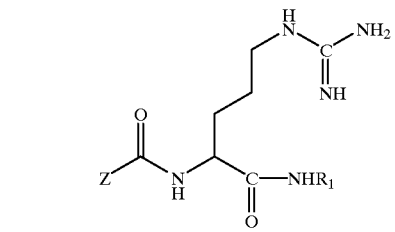

wherein $R_1$ is
  a) aryl, optionally substituted with $C_{1-4}$ alkyl, $C_{1-4}$ alkoxy, $C_{1-4}$ alkythio, halo, or —$NH_2$,
  b) —$(CH_2)_i$—aryl, in which aryl is substituted with $C_{1-4}$ alkyl, $C_{1-4}$ alkoxy, $C_{1-4}$ alkythio, halo, or —$NH_2$, or
  c) thienyl, furyl, pyridyl, benzofuranyl, or benzothienyl;
Z is $R_2$, or —$CHWR_2$;
$R_2$ is
  a) aryl, optionally substituted with one or two $C_{1-4}$ alkyl, $C_{1-4}$ alkoxy, $C_{1-4}$ alkythio, halo, —$NH_2$, $C_{1-4}$ alkylamino, $C_{1-4}$ dialkylamino, or —NHOH,
  b) $C_{1-4}$ alkyl, optionally substituted with fluoro,
  c) $C_{1-4}$ alkoxy,
  d) $C_{1-4}$ alkythio,
  e) halo, or
  f) thienyl, furanyl, or pyridyl;
W is H, —$NH_2$, $C_{1-4}$ alkylamino, $C_{1-4}$ dialkylamino, halo, hydroxyl, $C_{1-4}$ alkoxy, $C_{1-4}$ alkylthio, or azaheterocycle;
aryl is phenyl, or naphthyl;
azaheterocycle is n-morpholinyl, n-piperazinyl, n-pyrrolidinyl, n-imidazolyl, n-pyrrolyl, n-pyrazolyl, n-triazolyl, or n-tetrazolyl;
i is 0, 1, or 2;
wherein the oxazolidinone is a compound of structure IV

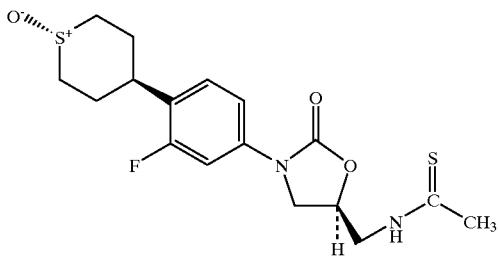

and a pharmaceutically acceptable salt.

4. The method of claim 1, 2, or 3 wherein the arginine derivative of formula A is L-phenylalanyl-Larginyl-β-naphthylamide.

5. The method of claim 1 or 3 wherein the oxazolidinone antibacterial agent and the arginine derivative of formula A are administered in a ratio of 10 (the oxazolidinone antibacterial agent) : 0.01 (the arginine derivative of formula A).

6. The method of claim 1 or 3 wherein the oxazolidinone antibacterial agent and the arginine derivative of formula A are administered in a ratio of 1:1.

7. The method of claim 1 and 3 wherein the effective amount of oxazolidinone antibacterial agent is from about 0.1 to about 100 mg/kg of body weight/day.

8. The method of claim 1 and 3 wherein the effective amount of oxazolidinone antibacterial agent is from about 3 to about 50 mg/kg of body weight/day.

9. The method of claim 1 and 3 wherein the amount of the arginine derivative of formula A is from about 0.01 to about 100 mg/kg of body weight/day.

10. The method of claim 1 and 3 wherein the amount of the arginine derivative of formula A is from about 0.3 to about 50 mg/kg of body weight/day.

11. The method of claim 1 and 3 wherein the oxazolidinone antibacterial agent and the arginine derivative of formula A are administered simultaneously.

12. The method of claim 1 and 3 wherein the arginine derivative of formula A is administrated about one to four hours before the oxazolidinone antibacterial agent is administered.

13. The method of claim 1 and 3 wherein the effective amount of an oxazolidinone antibacterial agent and an arginine derivative of formula A are administered orally, parenterally, transdermally or topically.

14. The method of claim 1 and 3 wherein the gram-negative organisms are aerobic gram-negative organisms.

15. The method of claim 14 wherein the aerobic gram-negative organism is *E. coli, Haemophilus influenzae, Moraxella catarrhalis, Pseudomonas aeruginosa,* or *Klebsiella pneumoniae.*

* * * * *